(12) United States Patent
Mineo et al.

(10) Patent No.: US 7,999,014 B2
(45) Date of Patent: Aug. 16, 2011

(54) FLAME RETARDANT AND POLYMER COMPOSITION USING THE SAME

(75) Inventors: Ryota Mineo, Chiba (JP); Tomohiro Eto, Chiba (JP); Yosihiro Deyama, Chiba (JP); Hiroyuki Satou, Chiba (JP)

(73) Assignee: JNC Corporation, Tokyo (JP)

( * ) Notice: Subject to any disclaimer, the term of this patent is extended or adjusted under 35 U.S.C. 154(b) by 677 days.

(21) Appl. No.: 12/043,037

(22) Filed: Mar. 5, 2008

(65) Prior Publication Data

US 2008/0227884 A1 Sep. 18, 2008

(30) Foreign Application Priority Data

Mar. 15, 2007 (JP) ................................. 2007-066958

(51) Int. Cl.
*C08F 2/42* (2006.01)
*C08F 2/46* (2006.01)
*C08F 2/50* (2006.01)
*C08J 3/28* (2006.01)
*C09D 11/00* (2006.01)

(52) U.S. Cl. ............... 522/115; 522/71; 522/74; 522/76; 522/100; 522/113; 522/114; 522/135; 522/144; 522/120; 522/121; 522/134; 522/162; 522/150; 522/153; 522/168; 522/170; 522/171; 522/178; 522/182; 522/909; 987/30; 987/33; 987/37; 987/43; 428/411.1

(58) Field of Classification Search .................. 522/100, 522/113, 114, 115, 135, 134, 144, 120, 121, 522/162, 150, 153, 168, 170, 171, 178, 182, 522/909; 987/30, 33, 37, 43; 428/411.1
See application file for complete search history.

(56) References Cited

U.S. PATENT DOCUMENTS

| | | | |
|---|---|---|---|
| 2006/0257785 A1* | 11/2006 | Johnson | 430/270.1 |
| 2007/0179223 A1* | 8/2007 | Hiroshige et al. | 524/100 |
| 2008/0097000 A1* | 4/2008 | Fujii et al. | 522/109 |
| 2009/0292038 A1* | 11/2009 | Tsutomu | 522/38 |

FOREIGN PATENT DOCUMENTS

| | | | |
|---|---|---|---|
| JP | 59152922 A * | 8/1984 | |
| JP | 60-161993 | 8/1985 | |
| JP | 2001-106766 | 4/2001 | |
| JP | 2001-213889 | 8/2001 | |
| JP | 2002-121245 | 4/2002 | |
| JP | 2003-302642 | 10/2003 | |
| JP | 2004-091683 | 3/2004 | |
| JP | 2004091683 A * | 3/2004 | |
| JP | 2006-282757 | 10/2006 | |
| JP | 2006-307152 | 11/2006 | |
| JP | 2007094342 A * | 4/2007 | |
| WO | WO 2004/099272 | 11/2004 | |

OTHER PUBLICATIONS

Shi et al. Photopolymerization and thermal Behaviors of acrylated benzenephosphonates/epoxy acrylate as flame retardant resins. European Polymer Journal, 42, 2006, 2261-2269.*

* cited by examiner

*Primary Examiner* — Sanza L McClendon
(74) *Attorney, Agent, or Firm* — J.C. Patents (57) ABSTRACT

A flame retardant suitable for manufacturing a polymer composition is provided. The polymer composition is used for forming a cured film in which a balance among flame retardancy, adhesion, chemical resistance, heat resistance, and elasticity, and so on, is provided. A flame-retardant polymer composition with an excellent balance among the above properties is also provided. The flame retardant of the invention has a structure of Formula (1), (2), or (3):

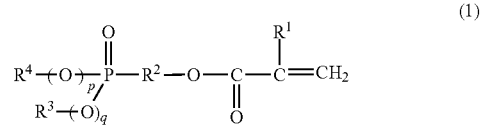

(1)

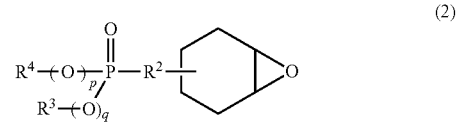

(2)

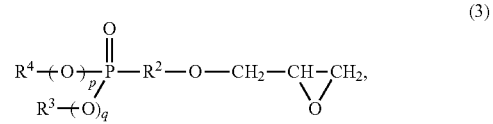

(3)

(in which, $R^1$ is hydrogen or methyl, $R^2$ is C2-20 alkylene or C2-20 alkylene in which any —$CH_2$— is replaced by —O—, $R^3$ and $R^4$ are C1-20 alkyl, phenyl, and phenyl substituted by C1-5 alkyl or phenyl, $R^3$ and $R^4$ may also be an integrally-formed cyclic group, and p and q are 0 or 1).

32 Claims, 3 Drawing Sheets

FLAME RETARDANT AND POLYMER COMPOSITION USING THE SAME

CROSS-REFERENCE TO RELATED APPLICATION

This application claims the priority benefit of Japanese application serial no. 2007-066958, filed Mar. 15, 2007. All disclosure of the Japanese application is incorporated herein by reference.

BACKGROUND OF THE INVENTION

1. Field of the Invention

The invention relates to a flame retardant and a polymer composition using the same, such as thermosetting composition, thermosetting inkjet ink, photo-curable composition, and photo-curable inkjet ink, in particular, to an inkjet ink for manufacturing liquid crystal display (LCD) devices, electroluminance display devices, printed circuit boards, and so on. Furthermore, the invention relates to a flame-retardant cured film formed by an inkjet ink, an electronic circuit board with a flame-retardant cured film formed thereon, and an electronic component with the electronic circuit board.

2. Description of Related Art

Generally, in order to ensure safety, the electronic circuit boards are required to use flame-retardant materials. Various bromides have been used previously for flame retardancy. However, due to the Dioxin problem occurring during combustion, a flame retardant free of bromides is needed. Currently, electronic components are required to have an increased heat resistance, and thus a flame retardant having a reactive functional group is needed. In this case, a variety of reactive flame retardants have been proposed (with reference to, for example, Japanese Laid-Open Patent Applications S60-161993, 2001-106766, 2001-213889, 2002-121245, and 2004-91683, and so on). However, the flame retardants described in the above patents are compounds obtained from the reaction of phosphorus-containing compounds and double bond of acryl; and thus, the variation range of the materials is rather narrow, which is difficult to balance among adhesion, chemical resistance, heat resistance, and elasticity required for the electronic circuit boards. On the other aspect, in recent years, when an electronic circuit board is being manufactured, an ink-jet printing process has been proposed as a method for forming a patterned cured film. The ink-jet printing process can provide the advantages of lower capital investment on equipments and higher material utilization efficiency, and a composition (an ink-jet ink) used in the method has also been proposed (with reference to, for example, Japanese Laid-Open Patent Application 2003-302642, WO 2004/099272 pamphlet, Japanese Laid-Open Patent Applications 2006-282757, and 2006-307152).

However, the cured films formed by these inkjet inks do not have sufficient flame retardancy.

SUMMARY OF THE INVENTION

Problems to be Solved by the Invention

Accordingly, a flame retardant suitable for manufacturing a polymer composition is needed. The polymer composition is used for forming a cured film in which a balance among the flame retardancy, adhesion, chemical resistance, heat resistance, and elasticity, and so on, can be achieved. A flame-retardant polymer composition, in which an excellent balance among the above properties can be achieved, is also needed.

Technical Means for Solving the Problems

The inventor of the invention has identified the following facts. A composition prepared by a flame retardant with a specific structure is suitable for forming a cured film in which a balance among flame retardancy, adhesion, chemical resistance, heat resistance, and elasticity, and so on, is achievable. Furthermore, the cured film formed by the polymer composition containing the flame retardant affords an excellent balance among the flame retardancy, adhesion, chemical resistance, heat resistance, and elasticity, and so on, is achievable. Accordingly, the inventor complete the invention based upon such knowledge and idea.

The invention provides a flame retardant and further provides a polymer composition, such as thermosetting composition, thermosetting inkjet ink, photo-curable composition, and photo-curable inkjet ink.

[1] A compound of Formula (1), (2), or (3):

1p;1.5p (in which, $R^1$ is hydrogen or methyl, $R^2$ is C2-20 alkylene in which —$CH_2$— may be replaced by —O—, $R^3$ and $R^4$ are independently C1-20 alkyl, phenyl, phenyl having at least one hydrogen replaced by C1-5 alkyl, or phenyl having at least one hydrogen replaced by phenyl, $R^3$ and $R^4$ may also be an integrally-formed cyclic group, and p and q are independently 0 or 1).

[2] A compound of Formula (4), (5), or (6):

(5)

(6)

(in which R¹ is hydrogen or methyl, and R² is C2-20 alkylene in which —CH$_2$— may be replaced by —O—).

[3] A thermosetting composition, containing: a flame retardant (A) selected from a compound of item [1] or [2], and a compound (B) with two or more oxiranes or oxetanes.

[4] A thermosetting inkjet ink, containing: a flame retardant (A) selected from a compound of item [1] or [2], and a compound (B) with two or more oxiranes or oxetanes.

[5] A photo-curable composition, containing: a flame retardant (A) selected from a compound of item [1] or [2], multifunctional (meth)acrylate (C), and a photo-polymerization initiator (D).

[6] A photo-curable inkjet ink, containing a flame retardant (A) selected from a compound of item [1] or [2], multifunctional (meth)acrylate (C), and a photo-polymerization initiator (D).

[7] The thermosetting composition according to item [3] or the thermosetting inkjet ink according to item [4], in which the compound (B) with two or more oxiranes or oxetanes is a compound of Formula (7), (8), (9), or (10), (7)

(8)

(9)

(10)

(in Formula (7), n is an integer of 0-10).

[8] The photo-curable composition according to item [5] or the photo-curable inkjet ink according to item [6], in which the multi-functional (meth)acrylate (C) is a compound of Formula (11), (in Formula (11), a number "r" of $R^5$ are groups of Formula (11-1), a number "s" of $R^5$ are groups of Formula (11-2), in which r is an integer of 1-5, s is an integer of 1-5, r+s is 6, and $R^1$ is hydrogen or methyl).

[9] The photo-curable composition according to item [5] or [8] or the photo-curable inkjet ink according to item [6] or [8], in which the photo-polymerization initiator (D) is bis(2,4,6-trimethylbenzoyl)phenyl phosphine oxide or 2,4,6-trimethyl-benzoyl-diphenyl phosphine oxide.

[10] The thermosetting composition according to item [3] or [7], the thermosetting inkjet ink according to item [4] or [7], the photo-curable composition according to item [5], [8], or [9], or the photo-curable inkjet ink according to item [6], [8], or [9], further contains monofunctional (meth)acrylate (E).

[11] The thermosetting composition, the thermosetting inkjet ink, the photo-curable composition, or the photo-curable inkjet ink according to item [10], in which the monofunctional (meth)acrylate (E) is a compound of Formula (12), (in which, $R^6$ is C2-12 alkylene which may have a ring structure, $R^1$ is hydrogen or methyl, and t is an integer of 1-30).

[12] The thermosetting composition, the thermosetting inkjet ink, the photo-curable composition, or the photo-curable inkjet ink according to item [11], in which the monofunctional (meth)acrylate (E) is at least one of 2-hydroxyethyl (meth)acrylate, 2-hydroxypropyl (meth)acrylate, 4-hydroxybutyl (meth)acrylate, 1,4-cyclohexanedimethanol mono(meth)acrylate and a combination thereof.

[13] The photo-curable inkjet ink according to item [6], in which the flame retardant (A) is at least one of the compound of Formula (4) in which $R^2$ is C3-5 alkylene, the compound of Formula (5) in which $R^2$ is ethylene, and the compound of Formula (6) in which $R^2$ is propylene; the multi-functional (meth)acrylate (C) is the compound of Formula (11); the photo-polymerization initiator (D) is any one of bis(2,4,6-trimethylbenzoyl)phenyl phosphine oxide or 2,4,6-trimethyl-benzoyl-diphenyl phosphine oxide; and the monofunctional (meth)acrylate (E) is 4-hydroxybutyl (meth)acrylate.

[14] The thermosetting composition according to item [3], [7], [10], [11], or [12], the thermosetting inkjet ink according to item [4], [7], [10], [11], or [12], the photo-curable composition according to item [5], [8], [9], [10], [11], or [12], or the photo-curable inkjet ink according to item [6], [8], [9], [10], [11], [12], or [13], in which a solvent with a boiling point of 300° C. or less under a normal pressure is not contained, or the ratio of a solvent with a boiling point of 300° C. or less under a normal pressure is 10 wt % or less of the whole composition.

[15] An electronic circuit board includes a flame-retardant cured film and a substrate, wherein the film on the substrate is fabricated using the thermosetting composition according to item [3], [7], [10], [11], [12], or [14], the thermosetting inkjet ink according to item [4], [7], [10], [11], [12], or [14], the photo-curable composition according to item [5], [8], [9], [10], [11], [12], or [14], or the photo-curable inkjet ink according to item [6], [8], [9], [10], [11], [12], [13], or [14].

[16] An electronic component is provided with the electronic circuit board according to item [15].

[17] A display device is provided with the electronic component according to item [16].

Furthermore, in this specification, "(meth)acrylate" indicates both "acrylate" and "methacrylate".

Effects of the Invention

The cured filmed formed by the polymer composition, such as thermosetting composition, thermosetting inkjet ink, photo-curable composition, and photo-curable inkjet ink, through using the flame retardant of the embodiments of the invention has an excellent balance among flame retardancy, adhesion, chemical resistance, heat resistance, and elasticity is achieved. Further, the cured filmed formed by the polymer composition of the invention is capable of serving as a material for manufacturing an electronic circuit board appropriately and safely.

In order to make the objectives, features, and advantages of the invention clearer and more comprehensible, the following embodiments are illustrated below in detail with reference to the appended drawings.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the embodiments of the invention, examples of which are illustrated in the accompanying drawings. Wherever possible, the same reference numbers are used in the drawings and the description to refer to the same or like parts.

1 Flame Retardant of the Invention

The flame retardant of the invention is a compound of Formula (1), (2), or (3), and preferably a compound of Formula (4), (5), or (6), and more preferably a compound of Formula (13), (14), or (15):

(13)

(14)

(15)

The compounds have a high content of phosphorus in the molecules and have a desirable flame retardancy. Furthermore, the compounds have a thermosetting reactive group such as (meth) acryloyl or oxirane at the end of the molecules, which thus are not bleed out even if they are heated at a high temperature. Therefore, if the compounds are applied in a cover lay of an electronic circuit board, the electronic circuit board will have excellent flame retardancy, adhesion, and chemical resistance properties. Furthermore, the compounds have smaller molecular weight, compared with the conventional flame retardants; thus, the viscosity thereof can be easily adjusted even if a large amount of the compounds are applied. Therefore, the compounds are suitable for being applied in a solvent-free inkjet ink with a viscosity adjusted to 2-200 mPa·s. The compounds are also suitable for being applied in an ink for screen printing with a viscosity adjusted to 1 Pa·s or more.

2. Thermosetting Composition of the Invention

Preferably, the thermosetting composition of the invention is prepared by mixing, dissolving, and filtering the flame retardant (A) of Formula (1), (2), or (3) and the compound (B) with two or more oxiranes or oxetanes. A fluorine resin membrane filter is used during filtering. The thermosetting composition may be used as the inkjet ink and the ink for screen printing.

2.1 Flame Retardant (A)

The flame retardant (A) used in the thermosetting composition of the invention is a compound of Formula (1), (2), or (3), and preferably a compound of Formula (4), (5), or (6), and more preferably a compound of Formula (13), (14), or (15). If the thermosetting composition contains the flame retardant (A), the formed cured film has high flame retardancy. Preferably, the content of the flame retardant (A) is 10 wt % or more based on the total weight of the thermosetting composition except the solvent, and thus, the thermosetting composition has improved flame retardancy. Considering the balance with other properties, the content of the flame retardant (A) is preferably 10 wt %-70 wt % based on the total weight of the thermosetting composition except the solvent.

2.2 Compound (B) with Two or More Oxiranes or Oxetanes

In order to obtain a cured film with high chemical resistance, the compound (B) with two or more oxiranes or oxetanes used in the thermosetting composition of the invention is preferably a multi-functional epoxy resin. The epoxy resin used in the invention includes, for example, bisphenol A exposy resin, glycidyl ester epoxy resin, and alicyclic epoxy resin. The epoxy resin includes, for example, the products with Trade Name of Epikote 807, Epikote 815, Epikote 825, Epikote 827, Epikote 828, Epikote 190P, Epikote 191P (manufactured by Yuka-Shell Epoxy Co., Ltd); the products with Trade Name of Epikote 1004, Epikote 1256 (manufactured by Japan Epoxy Resins Co., Ltd); the products with Trade Name of Araldite CY177, Araldite CY184 (manufactured by Japan Ciba-Geigy Co., Ltd); the products with Trade Name of Celloxide 2021P, EHPE-3150 (manufactured by Diacel Chemical Industries Co., Ltd); the products with Trade Name of Techmore VG3101L (manufactured by Mitsui Chemicals Co., Ltd), and so on. The mixture of the compound of Formula (7) Epikote 828, the compound of Formula (8) Araldite CY184, the compound of Formula (9) Techmore VG3101L, or the compound of Formula (10) Celloxide 2021P have high heat resistance and chemical resistance, and thus they are preferred.

Preferably, the content of the compound (B) with two or more oxiranes or oxetanes is 10 wt % or more based on the total weight of the thermosetting composition except the solvent, and thus the thermosetting composition will have an improved chemical resistance. Considering the balance with other properties, the compound (B) with two or more oxiranes or oxetanes is preferably 10 wt %-50 wt % based on the total weight of the thermosetting composition except the solvent.

2.3 Monofunctional (Meth)acrylate (E)

In order to be adjusted to a viscosity required by the application, the thermosetting composition of the invention may contain monofunctional (meth)acrylate (E). The specific examples of the monofunctional (meth)acrylate include, for example, glycidyl (meth)acrylate, 3,4-epoxycyclohexyl (meth)acrylate, methylglycidyl (meth)acrylate, 3-methyl-3-(meth)acryloxymethyloxetane, 3-ethyl-3-(meth)acryloxymethyloxetane, 3-methyl-3-(meth)acryloxyethyloxetane, 3-ethyl-3-(meth)acryloxyethyloxetane, p-vinylphenyl-3-ethyl epoxyprop-3-yl-methyl ether, 2-phenyl-3-(meth)acryloxymethyloxetane, 2-trifluoromethyl-3-(meth)acryloxymethyloxetane, 4-trifluoromethyl-2-(meth)acryloxymethyloxetane, (meth)acrylate, methyl (meth)acrylate, ethyl (meth)acrylate, isopropyl (meth)acrylate, butyl (meth)acrylate, iso-butyl (meth)acrylate, t-butyl (meth)acrylate, cyclohexyl (meth)acrylate, benzyl (meth)acrylate, styrene, methyl styrene, chloro-methyl styrene, (3-ethyl-3-oxetanyl)methyl (meth)acrylate, N-cyclohexyl maleimide, N-phenyl maleimide, vinyltoluene, tricyclo[5.2.1.0$^{2,6}$]decanyl (meth)acrylate, dicyclopentenyloxyethyl (meth)acrylate, isobornyl (meth)acrylate, phenyl (meth)acrylate, glycerol mono(meth)acrylate, polystyrene macromonomer, polymethyl methacrylate macromonomer, 5-tetrahydrofurfuryloxycarbonylpentyl (meth)acrylate, (meth)acrylate of ethylene oxide adduct of lauryl alcohol, (meth)acrylic acid, crotonic acid, α-chloroacrylic acid, cinnamic acid, maleic acid, fumaric acid, itaconic acid, citraconic acid, mesaconic acid, ω-carboxyl polycaprolactone mono(meth)acrylate, mono[2-(methyl)acryloxyethyl]succinate, mono[2-(methyl) acryloxyethyl]maleate, mono[2-(methyl)acryloxyethyl]cyclohexylene-3,4-dicarboxylate, (meth)acrylamide, N,N-dimethyl (meth)acrylamide, N,N-diethyl (meth)acrylamide, N,N-dimethylamine propyl(meth)acrylamide, N-isopropyl (meth)acrylamide, N-acryloyl morpholine, N-phenyl maleimide, N-cyclohexyl maleimide, 2-hydroxyethyl(meth)acrylate, 2-hydroxypropyl(meth)acrylate, 4-hydroxybutyl(meth) acrylate, 1,4-cyclohexanedimethol mono(meth)acrylate, and N-hydroxyethyl(meth)acrylamide.

Considering the high adhesion of the cured film with the substrate, 2-hydroxyethyl(meth)acrylate, 2-hydroxypropyl (meth)acrylate, 4-hydroxybutyl(meth)acrylate, 1,4-cyclohexanedimethol mono(meth)acrylate are preferred.

Preferably, the monofunctional (meth)acrylate (E) is 10 wt % or more based on the total weight of the thermosetting composition that excludes the solvent. Thus, the thermosetting composition can be adjusted to a viscosity required by the application. Considering the balance with other properties, the monofunctional (meth)acrylate (E) is preferably 10 wt %-70 wt % based on the total weight of the thermosetting composition except the solvent.

2.4 Other Components

In the thermosetting composition of the invention, a solvent for adjusting the viscosity, an epoxy curing agent for improving the heat resistance, a surfactant for improving the uniformity of the film surface, and a coupling agent for improving the adhesion with the substrate may also be added.

2.4.1 Solvent

The thermosetting composition of the invention may also contain a solvent for adjusting the viscosity required by the application. Preferably, the solvent contained in the thermosetting composition of the invention has a boiling point of 100° C.-300° C.

The specific examples of the solvent with a boiling point of 100° C.-300° C. include, for example, water, butyl acetate, butyl propionate, ethyl lactate, methyl oxyacetate, ethyl oxyacetate, butyl oxyacetate, methyl methoxyacetate, ethyl methoxyacetate, butyl methoxyacetate, methyl ethoxyacetate, ethyl ethoxyacetate, methyl 3-oxypropionate, ethyl 3-oxypropionate, methyl 3-methoxypropionate, ethyl 3-methoxypropionate, methyl 3-ethoxypropionate, ethyl 3-ethoxypropionate, methyl 2-oxypropionate, ethyl 2-oxypropionate, propyl 2-oxypropionate, methyl 2-methoxypropionate, ethyl 2-methoxypropionate, propyl 2-methoxypropionate, methyl 2-ethoxypropionate, ethyl 2-ethoxypropionate, methyl 2-oxy-2-methylpropionate, ethyl 2-oxy-2-methylpropionate, methyl 2-methoxy-2-methylpropionate, ethyl 2-ethoxy-2-methylpropionate, methyl pyruvate, ethyl pyruvate, propyl pyruvate, methyl acetoacetate, ethyl acetoacetate, methyl 2-oxobutyrate, ethyl 2-oxobutyrate, dioxane, ethylene glycol, diethylene glycol, triethylene glycol, propylene glycol, dipropylene glycol, tripropylene glycol, 1,4-butanediol, ethylene glycol monoisopropyl ether, ethylene glycol monobutyl ether, propylene glycol monomethyl ether, propylene glycol monomethyl ether acetate, propylene glycol monoethyl ether acetate, propylene glycol monopropyl ether acetate, dipropylene glycol monoethyl ether acetate, dipropylene glycol monobutyl ether acetate, ethylene glycol monobutyl ether acetate, cyclohexanone, cyclopentanone, diethylene glycol monomethyl ether, diethylene glycol monomethyl ether acetate, diethylene glycol monoethyl ether, diethylene glycol monoethyl ether acetate, diethylene glycol monobutyl ether, diethylene glycol monobutyl ether acetate, diethylene glycol dimethyl ether, diethylene glycol diethyl ether, diethylene glycol methylethylether, toluene, xylene, anisole, γ-butyrolatone, N,N-dimethylacetamide, N-methyl-2-pyrrolidone, dimethyl imidazolidone.

The solvent may be a single compound, and may also be a mixture of two or more different compounds. Preferably, in the thermosetting composition of the invention, the concentration of the solid ingredient of the solvent is 20 wt % or less.

2.4.2 Epoxy Curing Agent

The thermosetting composition of the invention may also contain an epoxy curing agent for improving the heat resistance of the cured film. The epoxy curing agent includes anhydrides curing agent, polyamines curing agent, polyphenols curing agent, and catalysts curing agent. Considering coloring and heat resistance, the anhydrides curing agent is better.

The specific examples of the anhydrides curing agent include, for example, maleic anhydride, tetrahydrophthalic anhydride, hexahydrophthalic anhydride, methyl hexahydrophthalic anhydride, hexahydrotrimellitic anhydride, phthalic anhydride, trimellitic anhydride, and styrene-maleic anhydride copolymer. The trimellitic anhydride and hexahydrotrimellitic anhydride with excellent heat resistance are preferred.

Preferably, the epoxy curing agent is 5 wt % or more based on the total weight of the thermosetting composition that excludes the solvent. Thus, the thermosetting composition has an improved heat resistance. Considering the balance with other properties, the epoxy curing agent is preferably 5 wt %-30 wt % based on the total weight of the thermosetting composition that excludes the solvent.

2.4.3 Surfactant

The thermosetting composition of the invention may also contain a surfactant for improving the wetting ability for the substrate and the uniformity of the surface of the cured film. The surfactant may be silicon-based surfactant, acrylic surfactant, and fluoro-based surfactant, and so on. The specific examples of the surfactant include, for example, silicon-based surfactants such as Byk-300, Byk-306, Byk-335, Byk-310, Byk-341, Byk-344, and Byk-370 (Trade Name, manufactured by BYK-Chemie Co., Ltd); acrylic surfactants such as Byk-354, ByK-358, and Byk-361 (Trade Name, manufactured by BYK-Chemie Co., Ltd); and DFX-18, Ftergent 250, and Ftergent 251 (Trade Name, manufactured by Neos Co., Ltd).

Preferably, the content of the surfactant is 0.01 wt % or more in the thermosetting composition, and thus, the uniformity of the surface of the cured film will be improved. Considering the balance with other properties, the surfactant is preferably 0.01 wt %-1 wt % of the thermosetting composition.

2.4.4 Coupling Agent

The thermosetting composition of the invention may also contain a coupling agent for improving the adhesion with the substrate. The coupling agent may be silane-based compounds, aluminum-based compounds, and titanates compounds. The specific examples of the coupling agent include, for example, silane-based compounds, such as 3-glycidoxypropyl dimethylethoxysilane, 3-glycidoxypropyl methyldiethoxysilane, and 3-glycidoxypropyl trimethoxysilane; aluminum-based compounds, such as acetalkoxyaluminium diisopropylate; and titanates compounds, such as tetraisopropylbis(dioctylphosphate)titanate. Among the compounds, 3-glycidoxypropyl trimethoxysilane has desirable effect in improving adhesion, which thus is preferred.

Preferably, the content of the coupling agent is 0.5 wt % or more based on the total weight of the thermosetting composition except the solvent, and thus, the thermosetting composition has an improved adhesion with the substrate. Considering the balance with other properties, the coupling agent is preferably 0.5 wt %-10 wt % based on the total weight of the thermosetting composition except the solvent.

2.4.5 Colorant

The thermosetting composition of the invention may contain a colorant for easily distinguishing the cured film from the substrate when the state of the cured film is examined. The colorant is preferably a pigment with desirable heat resistance. Preferably, the content of the colorant is 1 wt % or more in the thermosetting composition, and in this way, the cured film can be easily examined. Considering the balance with other properties, the colorant is preferably 1 wt %-10 wt % of the thermosetting composition.

2.4.6 Polymerization Inhibitor

The thermosetting composition of the invention may contain a polymerization inhibitor for improving the storage stability. The specific examples of the polymerization inhibitor include, for example, 4-methoxyphenol, hydroquinone, phenothiazine. Among the compounds, phenothiazine is preferred, since it can make the thermosetting composition to have smaller changes in viscosity during the long-term storage. The polymerization inhibitor may be a single compound, and may also be a mixture of two or more different compounds. Preferably, the content of the polymerization inhibitor is 0.01 wt % or more in the thermosetting composition, and thus, the thermosetting composition has smaller changes in viscosity during the long-term storage. Considering the balance with other properties, the polymerization inhibitor is preferably 0.01 wt %-1 wt % of the thermosetting composition.

3. Thermosetting Inkjet Ink of the Invention

If the viscosity of the thermosetting composition described in Section 2 is adjusted to 2 mPa·s-200 mPa·s at 25° C., it can serves as a thermosetting inkjet ink. When being used as an inkjet ink, it can be used to depict the desired patterns, which thus is suitable for manufacturing electronic circuit boards. In order for the ink be stably jetted from the nozzle, the viscosity of the thermosetting composition at 25° C. is preferably 50 mPa·s or less.

When using an ink with a viscosity at 25° C. as 50 mPa·s or even higher, the inkjet nozzle is preferably heated. If the ink contains a solvent with a low boiling point, the solvent is likely to be evaporated when the inkjet nozzle is heated, and thus the viscosity of the ink is increased, which may further result in a blockage at the nozzle. To avoid these problems, the ink is preferably free of solvent, or contains a small amount of solvent at a content of 10 wt % or less. Furthermore, the ink preferably contains monofunctional (meth)acrylate (E).

When the inkjet nozzle is not heated, the viscosity of the ink can be adjusted by adding a solvent.

4. Photo-Curable Composition of the Invention

The photo-curable composition of the invention may be prepared by mixing, dissolving, and filtering the flame retardant (A) of Formula (1), (2), or (3), the multi-functional (meth)acrylate (C), and the photo-polymerization initiator (D). A fluorine resin membrane filter is used during filtering. The photo-curable composition may be used as inkjet ink and ink for screen printing.

4.1 Flame Retardant (A)

The structure and the content of the flame retardant (A) used in the photo-curable composition of the invention are preferably the same as that of the flame retardant described in Section 2.1.

4.2 Multi-Functional (Meth)acrylate (C)

The specific examples of the multi-functional (meth)acrylate (C) used in the photo-curable composition of the invention include, for example, isocyanuric acid ethylene oxide modified di(meth)acrylate, pentaerythritol di(meth)acrylate, pentaerythritol di(meth)acrylate monostearate, pentaerythritol tri(meth)acrylate, trimethylol propane di(meth)acrylate, dipentaerythritol di(meth)acrylate, dipentaerythritol tri (meth)acrylate, dipentaerythritol tetra(meth)acrylate, dipentaerythritol penta(meth)acrylate, bisphenol F ethylene oxide modified diacrylate, bisphenol A ethylene oxide modified diacrylate, polyethylene glycol diacrylate, polypropylene glycol diacrylate, 1,4-buatanediol diacrylate, 1,6-hexanediol diacrylate, 1,9-nonanediol diacrylate, 1,4-cyclohexanedimethol diacrylate, 2-n-butyl-2-ethyl-1,3-propanediol diacrylate, trimethylol propane tri(meth)acrylate, ethylene oxide modified trimethylol propane tri(meth)acrylate, propylene oxide modified trimethylol propane tri(meth)acrylate, epichlorohydrin modified trimethylol propane tri(meth)acrylate, di(trimethylol propane) tetra(meth)acrylate, glycerol tri (meth)acrylate, epichlorohydrin modified tri(meth)acrylate, diglycerine tetra(meth)acrylate, pentaerythritol tetra(meth) acrylate, dipentaerythritol hexa(meth)acrylate, ethylene oxide modified phosphoric acid tri(meth)acrylate, tris[(meth) acryloxyethyl]isocyanate, urethane(meth)acrylate, and multi-functional (meth)acrylate of Formula (11). Preferably, the multi-functional (meth)acrylate of Formula (11) is used, and thus, the cured film has an improved flame retardant.

The multi-functional (meth)acrylate (C) used in the invention may be a single compound, and may also be a mixture of two or more different compounds. For example, the multi-functional (meth)acrylate (C) used in the invention may be a mixture of multi-functional (meth)acrylate of Formula (11) with other polymeric monomers. Preferably, the content of the multi-functional (meth)acrylate (C) is 10 wt % or more based on the total weight of the thermosetting composition except the solvent, and the thermosetting composition may be cured upon being irradiated with a small amount of UV lights. Considering the balance with other properties, the multi-functional (meth)acrylate (C) is preferably 10 wt %-80 wt % based on the total weight of the thermosetting composition that excludes the solvent.

4.3 Photo-Polymerization Initiator (D)

The photo-polymerization initiator (D) used in the photo-curable composition of the invention is not particularly limited, as long as it is a compound capable of generating free radicals upon being irradiated with UV lights or visible lights. The specific examples of the photo-polymerization initiator (D) include, for example, benzophenone, Michler's ketone, 4,4'-bis(diethylamino)benzophenone, xanthone, thioxanthone, isopropyl xanthone, 2,4-diethyl thioxanthone, 2-ethyl anthraquinone, acetophenone, 2-hydroxy-2-methyl propiophenone, 2-hydroxy-2-methyl-4'-isopropyl propiophenone, 1-hydroxycyclohexylphenylketone, isopropyl benzoinether, isobutyl benzoinether, 2,2-diethoxyacetophenone, 2,2-dimethoxy-2-phenylacetophenone, camphorquinone, benzanthrone, 2-methyl-1-[4-(methylthio)phenyl]-2-morpholinopropane-1-one, ethyl 2-benzyl-2-dimethylamino-1-(4-morpholinophenyl)-butanone-1,4-dimethylamino-benzoate, isoamyl 4-dimethylaminobenzoate, 4,4'-di(t-butylperoxycarbonyl)benzophenone, 3,4,4'-tri(t-butylperoxycarbonyl)benzophenone, 3,3',4,4'-tetra(t-butylperoxycarbonyl)benzophenone, 3,3',4,4'-tetra(t-hexylperoxycarbonyl)benzophenone, 3,3'-di(methoxycarbonyl)-4,4'-di(t-butylperoxycarbonyl) benzophenone, 3,4'-di(methoxycarbonyl)-4,3'-di(t- butylperoxycarbonyl)benzophenone, 4,4'-di(methoxycarbonyl)-3,3'-di(t-butylperoxycarbonyl) benzophenone, 1,2-octanedione, 1-[4-(phenylthio)phenyl]-, 2-(o-benzoyloxime), 2-(4'-methoxystyryl)-4,6-bis(trichloromethyl)-s-triazine, 2-(3',4'-dimethoxystyryl)-4,6-bis(trichloromethyl)-s-triazine, 2-(2',4'-dimethoxystyryl)-4,6-bis(trichloromethyl)-s-triazine, 2-(2'-methoxystyryl)-4,6-bis(trichloromethyl)-s-triazine, 2-(4'-pentyloxystyryl)-4,6-bis(trichloromethyl)-s-triazine, 4-[p-N,N-di(ethoxycarbonylmethyl)]-2,6-di(trichloromethyl)-s-triazine, 1,3-bis(trichloromethyl)-5-(2'-chlorophenyl)-s-triazine, 1,3-bis(trichloromethyl)-5-(4'-methoxyphenyl)-s-triazine, 2-(p-dimethylaminostyryl)]benzoxazole, 2-(p-dimethylaminostyryl)]benzthiazole, 2-mercapto benzthiazole, 3,3'-carbonyl-bis(7-diethylaminocoumarin), 2-(o-chlorophenyl)-4,4',5,5'-tetraphenyl-1,2'-biimidazole, 2,2'-bis(2-chlorophenyl)-4,4',5,5'-tetra(4-ethoxycarbonylphenyl)-1,2'-biimidazole, 2,2'-bis(2,4-dichlorophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-trichlorophenyl)-4,4',5,5'-tetraphenyl-1,2'-biimidazole, 3-(2-methyl-2-dimethylaminopropionyl)carbazole, 3,6-bis(2-methyl-2-morpholinopropionyl)-9-n-dodecylcarbazole, 1-hydroxycyclohexylphenyl ketone, bis($\eta^5$-2,4-cyclopentadien-1-yl)-bis(2,6-difluoro-3-(1H-pyrrole-1-yl)phenyl)titanium, bis(2,4,6-trimethylbenzoyl)phenyl phosphine oxide, and 2,4,6-trimethylbenzoyl-diphenyl phosphine oxide. Preferably, bis(2,4,6-trimethylbenzoyl)phenyl phosphine oxide and 2,4,6-trimethylbenzoyl-diphenyl phosphine oxide are used, which are photo-polymerization initiators containing phosphorus atoms, and thus the cured film has an improved flame retardant.

The photo-polymerization initiator (D) used in the invention may be a single compound, and may also be a mixture of two or more different compounds. Preferably, the content of the photo-polymerization initiator (D) is 1 wt % or more based on the total weight of the thermosetting composition except the solvent, and the photo-curable composition may be cured by means of being irradiated with a small amount of UV lights. Considering the balance with other properties, the multi-functional (meth)acrylate (C) is preferably 1 wt %-20 wt % based on the total weight of the thermosetting composition except the solvent.

4.4 Monofunctional (Meth)acrylate (E)

The photo-curable composition of the invention may contain monofunctional (meth)acrylate (E) for adjusting the viscosity to meet the requirements for the applications, and maintaining the property of being curable upon being irradiated with a small amount of UV lights. The type and the content of monofunctional (meth)acrylate used in the photo-curable composition are preferably the same as that of monofunctional (meth)acrylate described in Section 2.3.

4.5 Other Components

In the photo-curable composition of the invention, a solvent for adjusting the viscosity, an epoxy resin for improving the chemical resistance, the epoxy curing agent for improving the heat resistance, the surfactant for improving the uniformity of the film surface, and the coupling agent for improving the adhesion with the substrate may also be added.

4.5.1 Solvent

The type and content of the solvent used in the photo-curable composition of the invention are preferably same as that of the solvent described in Section 2.4.1.

4.5.2 Epoxy Resin

The type and content of the epoxy resin used in the photo-curable composition of the invention are preferably the same as that of the epoxy resin described in Section 2.2.

4.5.3 Epoxy Curing Agent

The type and content of the epoxy curing agent used in the photo-curable composition of the invention are preferably the same as that of the epoxy curing agent described in Section 2.4.2.

4.5.4 Surfactant

The type and content of the surfactant used in the photo-curable composition of the invention are preferably the same as that of the surfactant described in Section 2.4.3.

4.5.5 Coupling Agent

The type and content of the coupling agent used in the photo-curable composition of the invention are preferably the same as that of the coupling agent described in Section 2.4.4.

4.5.6 Colorant

The type and content of the colorant used in the photo-curable composition of the invention are preferably the same as that of the colorant described in Section 2.4.5.

4.5.7 Polymerization Inhibitor

The type and content of the polymerization inhibitor used in the photo-curable composition of the invention are preferably the same as that of the polymerization inhibitor described in Section 2.4.6.

5. Photo-Curable Inkjet Ink of the Invention

If the viscosity of the photo-curable composition described in Section 4 is adjusted to 2 mPa·s-200 mPa·s at 25° C., it can be used as a photo-curable inkjet ink. When being used as an inkjet ink, it can be used to depict desired patterns, which thus is suitable for manufacturing electronic circuit boards. In order for the ink be stably jetted from the nozzle, the viscosity of the photo-curable composition at 25° C. is preferably 50 mPa·s or less.

When using an ink with a viscosity at 25° C. and 50 mPa·s or even higher, the inkjet nozzle is preferably heated. When heating the inkjet nozzle, if the ink contains a solvent with a low boiling point, the solvent is likely to be evaporated, and thus the viscosity of the ink is increased, which may further result in a blockage at the nozzle. To avoid these problems, the ink is preferably free of solvent, or contains a small amount of solvent at a content of 10 wt % or less. Furthermore, the ink preferably contains monofunctional (meth)acrylate (E).

When the inkjet nozzle is not heated, the viscosity of the ink can be adjusted by adding a solvent.

6 Formation of the Cured Film

The thermosetting composition is coated on a surface of a substrate through a well-known process, such as ink jet coating, screen printing, spin coating, roll coating, bar coating, and slit coating, and then heated in an oven at 150° C.-250° C. or heated by a hot plate for 10 min-60 min, to get the cured film of the invention. Epoxy resin is reacted upon being heated and thus forming a strong and solid film.

As for the photo-curable composition, it is coated on a surface of a substrate through the above process, and then irradiated with UV lights or visible lights, to get the cured film of the invention. The part of the composition being irradiated is cured due to the polymerization of acrylic monomer into a three-dimensional cross-linker. The photo-curable inkjet ink can effectively prevent the diffusion of the ink, and thus fine patterns can be depicted. When the UV lights are used for irradiation, the amount of UV irradiation is measured with the integrated light Meter UIT-201 equipped with an photo detector UVD-365PD (manufactured by Ushio INC. Co., Ltd), which is preferably 10 mJ/cm$^2$-1,000 mJ/cm$^2$. Preferably, the inkjet ink is heated in an oven at 150° C.-250° C. or heated by a hot plate and baked for 10-60 min, and thus, the heat resistance and chemical resistance are improved.

In the specification, the substrate is not specially limited, as long as it serves as an object for coating the thermosetting composition, the thermosetting inkjet ink, the photo-curable composition, or the photo-curable inkjet ink of the invention, and the shape of the substrate may be a flat plate or a curved plate.

Furthermore, a material of the substrate used in the invention includes, for example, but not limited to, polyester resin, such as polyethylene terephthalate (PET) and poly(butylene terephthalate) (PBT); polyolefin resin, such as polyethylene and polypropylene; plastic film, such as polyvinyl chloride, fluorine resin, acrylic resin, polyamide, polycarbonate, polyimide; cellophane, acetate, metal foil, laminated film of polyimide and metal foil, glassine paper having filling effect, parchment paper or filling processing paper of polystyrene, clay binder, polyvinyl alcohol, starch, carboxymethyl cellulose (CMC), and glass, etc. The material for forming the substrate may further include additives, for example, pigment, dye, antioxidant, anti-aging agent, filler, UV absorber, antistatic agent, and/or electromagnetic inhibitor, without negatively influencing the invention.

The thickness of the substrate is not specially limited, but generally about 10 μm-2 mm, which may be appropriately adjusted according to the actual usage, preferably 15 μm-500 μm, and more preferably 20 μm-200 μm.

Depending upon the actual requirements, easy-bonding treatments such as corona treatment, plasma treatment, blasting treatment, may be performed on the surface of the substrate with the cured film formed thereon, or an easy-bonding layer is disposed.

Hereinafter, the invention is further illustrated with reference to the following Examples, but the invention is not limited thereto.

EXAMPLES

Synthesis Example 1

Synthesis of Flame Retardant (A1)

Figure 1:
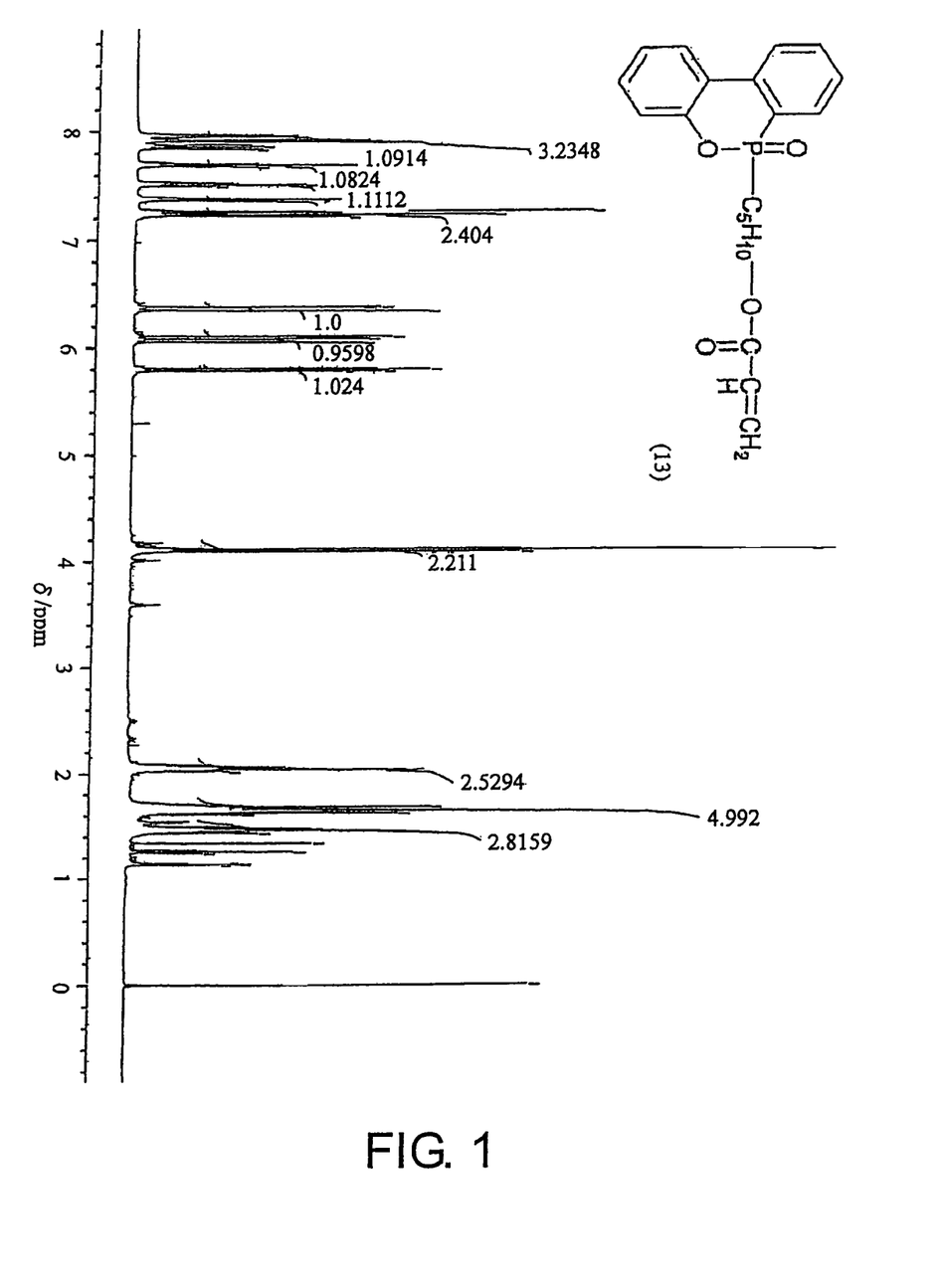
FIG. 1 shows an NMR spectrum of a compound of Formula (13) in Synthesis Example 1.

23.8 g of 9,10-dihydro-9-oxo-10-phosphaphenanthrene-10-oxide (hereinafter referred as HCA), 15 g of 4-penten-1-ol, 2.7 g of azobisisobutyronitrile, 110 mL of tetrahydrofuran were fed into a four-neck flask, and heated to reflux at 70° C. and stirred for 15 hr. Thereafter, the excessive raw materials and the solvent were vacuum distilled off at 100° C. for 3 hr. Then, 18 mL of triethylamine, 200 mL of tetrahydrofuran were added into the reactant, and the temperature was further decreased to 0° C. in a nitrogen atmosphere. Thereafter, 11 mL of acryloyl chloride was dropped in, and stirred at 20° C. for 2 hr. Then, a saturated solution of sodium hydrogen carbonate was added at 0° C., and the water layer of the resulted solution was extracted twice with ethyl acetate. The combined organic layer was washed with an aqueous solution of sodium chloride, and then was dried by adding sodium sulfate. Under reduced pressure, the solvent was distilled at 35° C., to get 41 g of the compound of Formula (13). The NMR spectrum thereof is shown in FIG. 1. The product is used as the flame retardant (A1).

Synthesis Example 2

Synthesis of Flame Retardant (A2)

Figure 2:
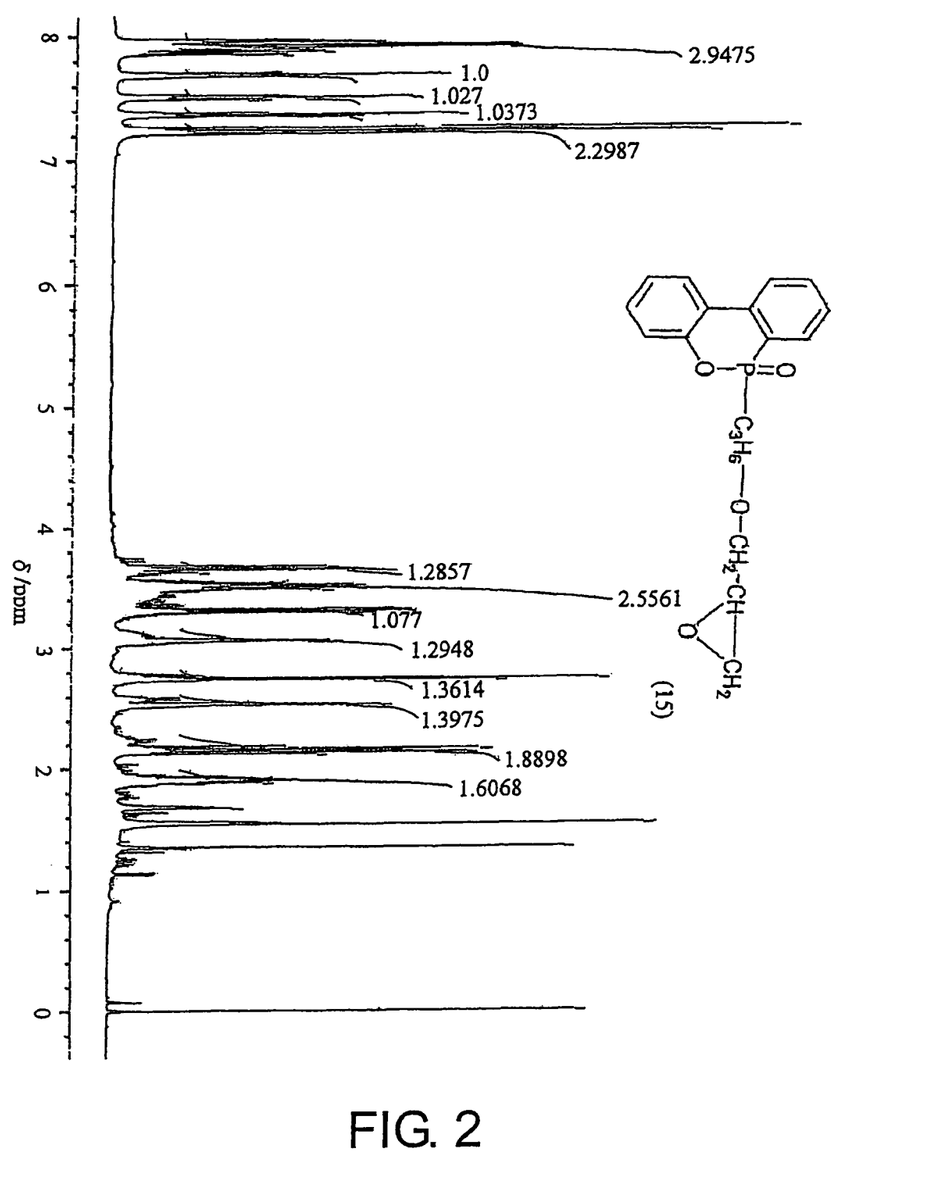
FIG. 2 shows an NMR spectrum of a compound of Formula (15) in Synthesis Example 2.

43.2 g of HCA, 43 g of allylglycidylether, 3.3 g of azobisisobutyronitrile, and 100 mL of 1,4-dioxane were fed into a four-neck flask, heated to 80° C., and stirred for 10 hr. Then, the excessive raw materials and the solvent was vacuum distilled off at 90° C. for 4 hr, to get 63 g of the compound of Formula (15). The NMR spectrum thereof is shown in FIG. 2. The product is used as the flame retardant (A2).

Synthesis Example 3

Synthesis of Flame Retardant (A3)

Figure 3:
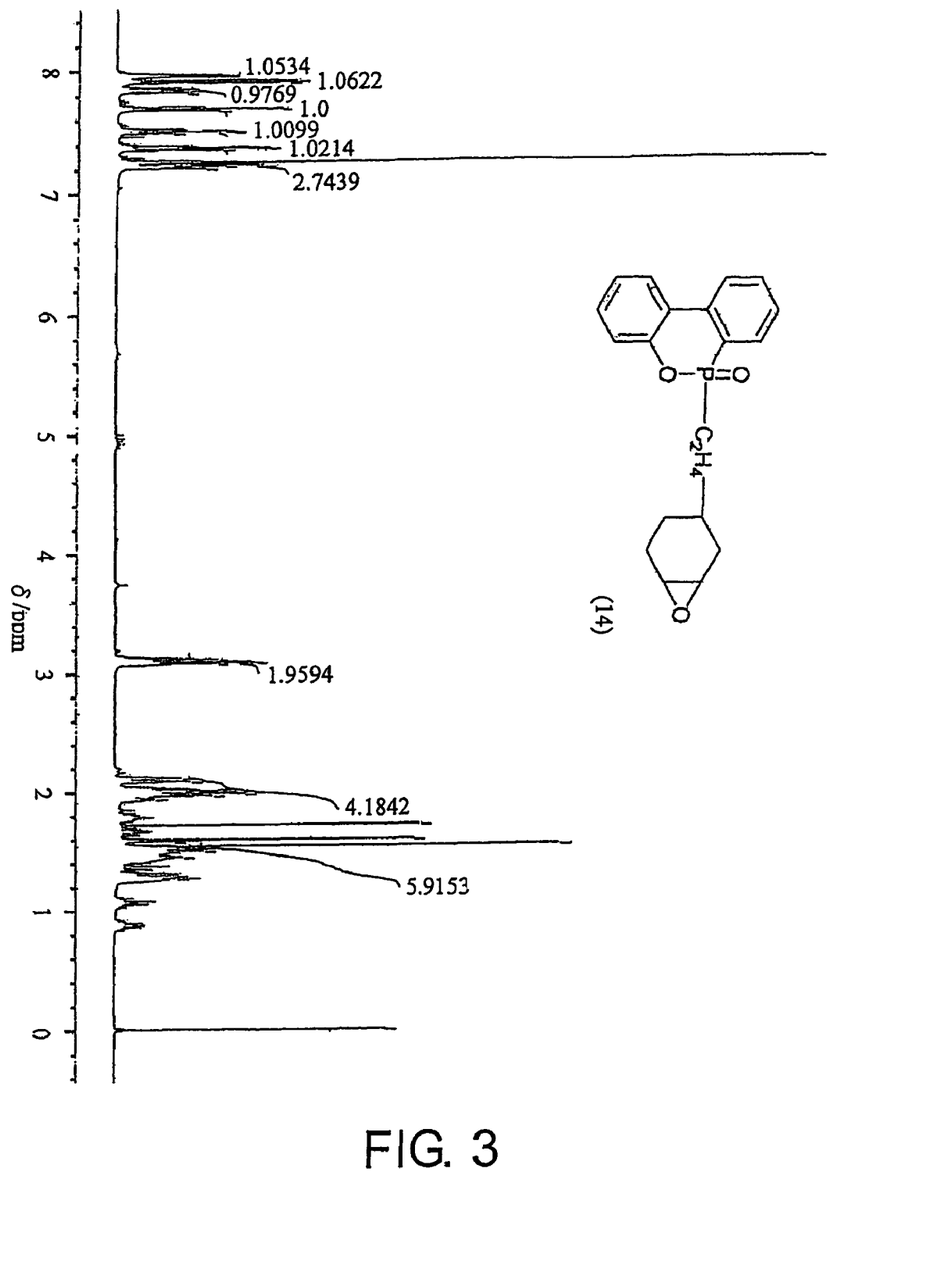
FIG. 3 shows an NMR spectrum of a compound of Formula (14) in Synthesis Example 3.

The process of Synthesis Example 2 was repeated, except that allylglycidylether was replaced by Celloxide 2000 (Trade Name, manufactured by Diacel Chemical Industries Co., Ltd), to get the compound of Formula (14). The NMR spectrum thereof is shown in FIG. 3. The product is used as the flame retardant (A3).

Synthesis Example 4

Synthesis of Flame Retardant (A4)

The process of Synthesis Example 2 was repeated, except that HCA was replaced by diphenyl phosphate, to get the compound of Formula (16), (16)

Synthesis Example 5

Synthesis of Flame Retardant (A5)

The process of Synthesis Example 2 was repeated, except that HCA was replaced by diisopropyl phosphate, to get the compound of Formula (17), (17)

Synthesis Example 6

Synthesis of Flame Retardant (A6)

The process of Synthesis Example 2 was repeated, except that HCA is replaced by diphenyl phosphate, to get the compound of Formula (18), (18)

Example 1

According to the following composition, the flame retardant (A1), HF-DPHA30 (Trade Name, manufactured by Showa Highpolymer Co., Ltd, a mixture of the addition product (the compound of Formula (11)) of dipentaerythritol hexaacrylate and HCA with propylene glycol monomethyl ether acetate at a weight ratio of 80:20, referred to as HF-DPHA hereinafter) as the multi-functional acrylate, 4-hydroxybutyl acrylate (referred to as 4HBA hereinafter) as the monofunctional acrylate, 2,4,6-trimethylbenzoyl-diphenylphosphine oxide (manufactured by Ciba Specialty Chemicals Co., Ltd, DAROCUR (Trade Name) TPO, referred to as TPO hereinafter) as the photo-polymerization initiator, and phenothiazine as the polymerization inhibitor were mixed and dissolved, and then filtered by a 0.2 μm membrane filter made of fluorine resin, to get a photo-curable inkjet ink 1.

| | |
|---|---|
| Flame Retardant (A1) | 32.00 g |
| HF-DPHA | 40.00 g |
| 4HBA | 100.00 g |
| TPO | 5.00 g |
| Phenothiazine | 0.02 g |

The photo-curable inkjet ink 1 was injected into an inkjet cartridge, and then the inkjet cartridge was installed in an inkjet device DMP-2811 (Trade Name, manufactured by Dimatix Company), so as to print on Kapton (registered trademark, Trade Name, Du Pont-Toray Co., Ltd, Thick 150 μm, Type H, referred to as Kapton substrate hereinafter) as the polyimide film. The printing conditions were set as the line width of 200 μm, and the line interval of 200 μm. It was coated for once, the line length was 50 mm, the jetting speed from the nozzle was 10 times per second, and the jetting temperature was 70° C.

At 30 mJ/cm², the printed substrate was irradiated by UV lights with a wavelength of 365 nm, and then baked at 190° C. for 30 min, to get a Kapton substrate 1 with lines and special patterns formed thereon. The substrate 1 was observed with a microscope to confirm that the lines had desirable linearity and thus the ink is confirmed to be suitable for coating on the substrate.

Then, the photo-curable inkjet ink 1 was coated on a template of 13 mm wide, 125 mm long, to reach a thickness of 5 mm, and then irradiated by 365 nm UV light at 30 mJ/cm2 for 20 times, so as to be cured. Then, the template was removed, and the cured film was baked at 190° C. for 30 min, to get a sample 1 for combustion test. The sample 1 for combustion test was placed close to the flame of a lighter. Meanwhile, the sample 1 was burnt when contacting the flame, and was extinguished within about 1 second after getting away from the flame. Therefore, it can be confirmed that the photo-curable inkjet ink 1 has flame retardancy.

Comparative Example 1

According to the following composition, dipentaerythritol hexaacrylate (referred to as DPHA hereinafter) as the multi-functional acrylate, 4HBA, TPO, and phenothiazine were mixed and dissolved, and then filtered by a 0.2 μm membrane filter made of fluorine resin, to get a photo-curable inkjet ink 2.

| | |
|---|---|
| DPHA | 80.00 g |
| 4HBA | 60.00 g |
| TPO | 5.00 g |
| Phenothiazine | 0.02 g |

The photo-curable inkjet ink 2 was coated, exposed, and baked through the same way as that in Example 1, to get a Kapton substrate 2. The substrate 2 was observed with a microscope to confirm that the lines had desirable linearity and thus the ink is confirmed to be suitable for inkjet coating on the substrate.

Then, the photo-curable inkjet ink 2 was used to prepare a sample 2 for combustion test through the same way as that in Example 1. The sample 2 for combustion test was placed close to the flame of a lighter. The flames became large and the sample 2 was burnt once the sample 2 contacted the flames, and the sample 2 still kept burning even it was removed from the flame. Therefore, it can be confirmed that the photo-curable inkjet ink 2 does not have flame retardancy.

Example 2

According to the following composition, the flame retardant (A2), Epikote 828 (Trade Name, manufactured by Epoxy Resins Co., Ltd, Japan) as epoxy resin, trimellitic anhydride as the epoxy curing agent were mixed and dissolved, and then filtered by a 0.2 μm membrane filter made of fluorine resin, to get a thermosetting composition 1.

| | |
|---|---|
| Flame Retardant (A2) | 70.00 g |
| Epikote 828 | 30.00 g |
| Trimellitic Anhydride | 10.00 g |

Then, the thermosetting composition 1 was coated on a template of 13 mm wide, and 125 mm long, to reach a thickness of 5 mm, and then baked at 200° C. for 30 min, so as to be cured. Then, the template was removed, to get a sample 3 for combustion test. The sample 3 for combustion test was placed close to the flame of a lighter. The sample 1 was burnt when contacting the flame, and was extinguished within about 1 second after being removed from the flame. Therefore, it can be confirmed that the thermosetting composition 1 has flame retardancy.

Comparative Example 2

According to the following composition, Celloxide 2021P (Trade Name, manufactured by Diacel Chemical Industries Co., Ltd.) and Epikote 828 (Trade Name, manufactured by Epoxy Resins Co., Ltd, Japan) as epoxy resin, trimellitic anhydride as the epoxy curing agent were mixed and dissolved, and then filtered by a 0.2 μm membrane filter made of fluorine resin, to get a thermosetting composition 2.

| | |
|---|---|
| Celloxide 2021P | 70.00 g |
| Epikote 828 | 30.00 g |
| Trimellitic Anhydride | 10.00 g |

Then, the thermosetting composition 2 was used to prepare a sample 4 for combustion test through the same way as that in Example 2. The sample 4 for combustion test was placed close to the flame of a lighter. The flames became large and the sample 4 was burnt once the sample 4 contacted the flames, and the sample 4 remained burning even if it was removed from the flame. Therefore, it can be confirmed that the thermosetting composition 2 does not have flame retardancy.

INDUSTRIAL APPLICATION

The flame retardant of the invention and the cured film formed by the inkjet ink using the flame retardant of the invention have excellent flame retardancy, and can be used as, for example, an etching resist, protective film, or insulating film used in electronic circuit boards.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A compound of Formula (1), (2), or (3), (1)

(2)

(3)

wherein $R^1$ is hydrogen or methyl, $R^2$ is C2-20 alkylene $R^3$ and $R^4$ are independently C1-20 alkyl, phenyl, phenyl with at least one hydrogen replaced by C1-5 alkyl, or phenyl with at least one hydrogen replaced by phenyl, $R^3$ and $R^4$ are also an integrally-formed cyclic group, and p and q are independently 0 or 1.

2. A compound of Formula (4), (5), or (6), (4)

(5)

(6)

wherein $R^1$ is hydrogen or methyl, and $R^2$ is C2-20 alkylene or C2-20 alkylene with at least one —$CH_2$— being replaced by —O—.

3. A thermosetting composition, comprising: a flame retardant (A) selected from the compound according to claim 1, and a compound (B) with two or more oxirane rings or oxetane rings.

4. A thermosetting composition, comprising: a flame retardant (A) selected from the compound according to claim 2, and a compound (B) with two or more oxirane rings or oxetane rings.

5. A thermosetting inkjet ink, comprising: a flame retardant (A) selected from the compound according to claim 1, and a compound (B) with two or more oxirane rings or oxetane rings.

6. A thermosetting inkjet ink, comprising: a flame retardant (A) selected from the compound according to claim 2, and a compound (B) with two or more oxirane rings or oxetane rings.

7. A photo-curable composition, comprising: a flame retardant (A) selected from the compound according to claim 1, multi-functional (meth)acrylate (C), and a photo-polymerization initiator (D).

8. A photo-curable composition, comprising: a flame retardant (A) selected from the compound according to claim 2, multi-functional (meth)acrylate (C), and a photo-polymerization initiator (D).

9. A photo-curable inkjet ink, comprising: a flame retardant (A) selected from the compound according to claim 1, multi-functional (meth)acrylate (C), and a photo-polymerization initiator (D).

10. A photo-curable inkjet ink, comprising: a flame retardant (A) selected from the compound according to claim 2, multi-functional (meth)acrylate (C), and a photo-polymerization initiator (D).

11. The thermosetting composition according to claim 3, wherein the compound (B) with two or more oxirane rings or oxetanes rings is a compound of Formula (7), (8), (9), or (10), (7)

(9)

(8)

(10)

wherein in Formula (7), n is an integer of 0-10.

12. The thermosetting composition according to claim 4, wherein the compound (B) with two or more oxirane rings or oxetane rings is a compound of Formula (7), (8), (9), or (10), (7)

(9)

(8)

wherein in Formula (7), n is an integer of 0-10.

13. The photo-curable composition according to claim 7, wherein the multi-functional (meth)acrylate (C) is a compound of Formula (11), wherein in Formula (11), a number "r" of $R^5$ among the six $R^5$-groups are groups of Formula (11-1), a number "s" of $R^5$ among the six $R^5$-groups are groups of Formula (11-2), r is an integer of 1-5, s is an integer of 1-5, r+s is 6, and $R^1$ is hydrogen or methyl.

14. The photo-curable composition according to claim 8, wherein the multi-functional (meth)acrylate (C) is a compound of Formula (11), wherein in Formula (11), a number "r" of $R^5$ among the six $R^5$-groups are groups of Formula (11-1), a number "s" of $R^5$ among the six $R^5$-groups are groups of Formula (11-2), r is an integer of 1-5, s is an integer of 1-5, r+s is 6, and $R^1$ is hydrogen or methyl.

15. The photo-curable composition according to claims 7, wherein the photo-polymerization initiator (D) is bis(2,4,6-trimethylbenzoyl)phenyl phosphine oxide or 2,4,6-trimethylbenzoyl-diphenyl phosphine oxide.

16. The photo-curable composition according to claims 8, wherein the photo-polymerization initiator (D) is bis(2,4,6-trimethylbenzoyl)phenyl phosphine oxide or 2,4,6-trimethylbenzoyl-diphenyl phosphine oxide.

17. The thermosetting composition according to claims 3, further comprising monofunctional (meth)acrylate (E).

18. The thermosetting composition according to claims 4, further comprising monofunctional (meth)acrylate (E).

19. The thermosetting composition according to claim 17, wherein the monofunctional (meth)acrylate (E) is a compound of Formula (12), wherein, $R^6$ is C2-12 alkylene which may have a ring structure, $R^1$ is hydrogen or methyl, and t is an integer of 1-30.

20. The thermosetting composition according to claim 18, wherein the monofunctional (meth)acrylate (E) is a compound of Formula (12), wherein, $R^6$ is C2-12 alkylene which may have a ring structure, $R^1$ is hydrogen or methyl, and t is an integer of 1-30.

21. The thermosetting composition according to claim 19, wherein the monofunctional (meth)acrylate (E) is at least one of 2-hydroxyethyl (meth)acrylate, 2-hydroxypropyl (meth)acrylate, 4-hydroxybutyl (meth)acrylate, 1,4-cyclohexanedimethanol mono(meth)acrylate, and a combination thereof.

22. The thermosetting composition according to claim 20, wherein the monofunctional (meth)acrylate (E) is at least one of 2-hydroxyethyl (meth)acrylate, 2-hydroxypropyl (meth)acrylate, 4-hydroxybutyl (meth)acrylate, 1,4-cyclohexanedimethanol mono(meth)acrylate, and a combination thereof.

23. The photo-curable inkjet ink according to claim 9, wherein the flame retardant (A) is at least one of the compound of Formula (4) with $R^2$ as C3-5 alkylene, the compound of Formula (5) with $R^2$ as ethylene, and the compound of Formula (6) with $R^2$ as propylene; the multi-functional (meth)acrylate (C) is the compound of Formula (11); the photo-polymerization initiator (D) is any one of bis(2,4,6-trimethylbenzoyl)phenyl phosphine oxide or 2,4,6-trimethyl-benzoyl-diphenyl phosphine oxide; and the monofunctional (meth)acrylate (E) is 4-hydroxybutyl (meth)acrylate, (4)

(5)

(6)

(11)

wherein in Formulae (4), (5) and (6), $R^1$ is hydrogen or methyl, and $R^2$ is C2-20 alkylene or C2-20 alkylene with at least one —$CH_2$— being replaced by —O—; and in Formula (11), a number "r" of $R^5$ among the six $R^5$-groups are groups of Formula (11-1), a number "s" of $R^5$ among the six $R^5$-groups are groups of Formula (11-2), r is an integer of 1-5, s is an integer of 1-5, and r+s is 6.

24. The photo-curable inkjet ink according to claim 10, wherein the flame retardant (A) is at least one of the compound of Formula (4) with $R^2$ as C3-5 alkylene, the compound of Formula (5) with $R^2$ as ethylene, and the compound of Formula (6) with $R^2$ as propylene; the multi-functional (meth)acrylate (C) is the compound of Formula (11); the photo-polymerization initiator (D) is any one of bis(2,4,6-trimethylbenzoyl)phenyl phosphine oxide or 2,4,6-trimethyl-benzoyl-diphenyl phosphine oxide; and the monofunctional (meth)acrylate (E) is 4-hydroxybutyl (meth)acrylate, (11)

(11-1)

(11-2)

wherein in Formula (11), a number "r" of $R^5$ among the six $R^5$-groups are groups of Formula (11-1), a number "s" of $R^5$ among the six $R^5$-groups are groups of Formula (11-2), r is an integer of 1-5, s is an integer of 1-5, r+s is 6, and $R^1$ is hydrogen or methyl.

25. The thermosetting composition according to claim 3, comprising no solvent with a boiling point of 300° C. or less under a normal pressure, or comprising a solvent with a boiling point of 300° C. or less under a normal pressure at a ratio of 10 wt % or less based on a total weight of the composition.

26. The thermosetting composition according to claim 4, comprising no solvent with a boiling point of 300° C. or less under a normal pressure, or comprising a solvent with a boiling point of 300° C. or less under a normal pressure at a ratio of 10 wt % or less based on a total weight of the composition.

27. An electronic circuit board, using the thermosetting composition according to claims 3 to form a flame-retardant cured film on a substrate.

28. An electronic circuit board, using the thermosetting composition according to claims 4 to form a flame-retardant cured film on a substrate.

29. An electronic component, provided with the electronic circuit board according to claim 27.

30. An electronic component, provided with the electronic circuit board according to claim 28.

31. A display device, provided with the electronic component according to 29.

32. A display device, provided with the electronic component according to 30.

* * * * *